US012674140B2

(12) United States Patent
Lin et al.

(10) Patent No.: US 12,674,140 B2
(45) Date of Patent: Jul. 7, 2026

(54) MYOGENIN-EXPRESSING FIBROBLAST-LIKE CELL (MEFLC) LINE AND CONSTRUCTION METHOD AND USE THEREOF

(71) Applicant: Foshan Zhongke Rhythm Biotech Co., Ltd., Foshan (CN)

(72) Inventors: Bin Lin, Foshan (CN); Weiwei Kong, Foshan (CN); Lishi Zhou, Foshan (CN); Ping Wang, Foshan (CN); Zebin Lin, Foshan (CN); Qiang Gao, Foshan (CN); Jianzheng Cen, Foshan (CN); Jian Zhuang, Foshan (CN)

(73) Assignee: FOSHAN ZHONGKE RHYTHM BIOTECH CO., LTD., Foshan (CN)

( * ) Notice: Subject to any disclaimer, the term of this patent is extended or adjusted under 35 U.S.C. 154(b) by 668 days.

(21) Appl. No.: 18/193,665

(22) Filed: Mar. 31, 2023

(65) Prior Publication Data

US 2024/0034997 A1      Feb. 1, 2024

(30) Foreign Application Priority Data

Jul. 29, 2022      (CN) .......................... 202210907968.7

(51) Int. Cl.
C12N 5/077      (2010.01)
C12N 15/86      (2006.01)

(52) U.S. Cl.
CPC ........... C12N 5/0656 (2013.01); C12N 15/86 (2013.01); *C12N 2500/84* (2013.01); *C12N 2506/45* (2013.01); *C12N 2740/15043* (2013.01)

(58) Field of Classification Search
None
See application file for complete search history.

(56) References Cited

PUBLICATIONS

AddGene pCW-Cas9-Blast, vector construction, p. 1-5 (Year: 2025).*
AddGene MYOG lentiviral human search results, p. 1-26 (Year: 2025).*
Addgene Plasmid #83481, pCW-Cas9-Blast, reference image for reasons for allowance (Year: 2025).*
Addgene search results for Myog human lentiviral plasmid, reference for reasons for allowance (Year: 2025).*

* cited by examiner

*Primary Examiner* — Christopher M Babic
*Assistant Examiner* — Hanna Marie Thueson
(74) *Attorney, Agent, or Firm* — Bayramoglu Law Offices LLC

(57)      ABSTRACT

A myogenin-expressing fibroblast-like cell (MEFLC) line and a construction method and a use thereof are provided. The MEFLC line was deposited in the Guangdong Microbial Culture Collection Center (GDMCC) on Apr. 23, 2022 with an accession number of GDMCC NO: 62409. The construction method includes: 1) constructing a pCW-MYOG-T2A-Puro lentivirus; 2) infecting a human induced pluripotent stem cell (iPSC) line with the lentivirus, inducing the expression of an MYOG gene, and screening out a positive monoclonal cell line; 3) subjecting the positive monoclonal cell line to expanded cultivation, during which the expression of the MYOG gene is continuously induced; and 4) changing cultivation conditions, continuously inducing the expression of the MYOG gene, and screening out positive monoclonal cell lines to ensure the purity of MYOG-positive cells until a cell morphology changes significantly into fibroblastoid cells to obtain the MEFLC line.

14 Claims, 5 Drawing Sheets

■HCFC ●MEFLC

MEFLC+hiPSC-CM hiPSC-CM

FIG. 7A                    FIG. 7B                    FIG. 7C

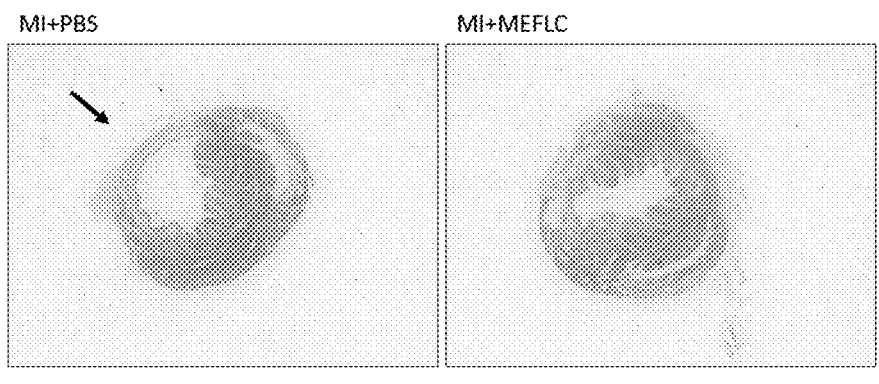
FIG. 8A                    FIG. 8B

MYOGENIN-EXPRESSING FIBROBLAST-LIKE CELL (MEFLC) LINE AND CONSTRUCTION METHOD AND USE THEREOF

CROSS REFERENCE TO THE RELATED APPLICATIONS

This application is based upon and claims priority to Chinese Patent Application No: 202210907968.7, filed on Jul. 29, 2022, the entire contents of which are incorporated herein by reference,

TECHNICAL FIELD

The present disclosure relates to a myogenin-expressing fibroblast-like cell (MEFLC) line and a construction method and use thereof.

BACKGROUND

Myocardial infarction (MI) refers to irreversible necrosis of cardiomyocytes in a corresponding blood supply area that is caused by an acute occlusion of coronary arteries. Cardiomyocytes are terminally differentiated cells, and thus, necrotized cardiomyocytes caused by hypoxic-ischemic injury (HII) cannot undergo self-repair through cell regeneration like other renewable cells but undergo fibrosis to produce scar tissue, thereby resulting in cardiac remodeling and gradual cardiac insufficiency. Embryonic stem cells (ESCs) can be used to replace cardiomyocytes lost after MI through myocardial regeneration to promote scar repair, which can avoid the development of heart failure due to cardiac remodeling. However, the use of ESCs has moral and ethical issues.

In recent years, the development of induced pluripotent stem cell (iPSC) technology has provided a new research direction for the entire stem cell biology field and clinical regenerative medicine. iPSCs have similar pluripotency to ESCs and can also avoid moral and ethical controversies. Therefore, the development of the iPSC technology and the establishment of cardiomyocyte differentiation and purification methods make it possible to prepare and cultivate human cardiomyocytes in vitro. At present, the research and use of the iPSC technology in cardiovascular diseases (CVDs) focus on the following two aspects: 1. Somatic cells of a CVD patient are programmed into iPSCs, and a disease model is then established in vitro to investigate the pathogenesis and an effective drug at a cellular level. 2. iPSCs or cardiomyocytes differentiated from iPSCs are transplanted into a patient to treat MI, heart failure, or the like.

In vivo experiments have confirmed that undifferentiated iPSCs can differentiate into cardiomyocytes in vivo, but such cells have a risk of tumorigenesis due to their ESC characteristics. Therefore, inducing iPSCs to differentiate into myocardial lineage cells in vitro and then transplanting the myocardial lineage cells into a heart may be a desired option to avoid the risk of tumorigenesis. Studies have confirmed that the injection of iPSC-derived cardiomyocytes (iPSC-CMs) into an MI area of an MI mouse can significantly improve the cardiac function of the MI mouse, and the transplantation of a cell slice obtained through co-cultivation of iPSC-CMs and endothelial cells into an MI site of an MI rat can also improve the cardiac function of the MI rat. However, the low survival rate of cells transplanted locally has always been a common problem of cell transplantation therapy, and the optimization of the survival time of cells in vivo is a key issue in clinical transformation.

The transcription factor gene MYOG encodes myogenin and is a member of the myogenic regulatory factor (MRF) gene family. The MRF family (including Myod, Myf5, Mrf4, and MYOG) plays a critical role in each stage of skeletal myogenesis. All members of this family share a conserved basic helix-loop-helix (bHLH) motif, which can bind to an E-box of a downstream gene, thereby activating the expression of a downstream muscle-specific gene. Studies have shown that MYOG plays a key role in muscle differentiation by controlling and initiating the fusion of myoblasts and the generation of muscle fibers. Studies in mice have shown that the deletion of the MYOG gene leads to severe defects in muscle differentiation, resulting in perinatal death. Therefore, MYOG is an essential regulatory factor for skeletal muscle development and is irreplaceable. At present, studies have confirmed that the MYOG gene is expressed in the hearts of mice, ducks, grass carp, Jinghai yellow chickens, and other animals, which may be related to the growth and development of myocardium. However, the expression of the MYOG gene in human cardiac tissues and the role of the MYOG gene in cardiac development have not been reported yet.

SUMMARY

The technical problem to be solved by the present disclosure is to provide an MEFLC line and a construction method and use thereof.

To solve the above technical problem, the present disclosure adopts the following technical solutions:

A deposit of the biological material described in the present application has been made in a depository affording permanence of the deposit and ready accessibility thereto by the public upon grant of a patent, namely the Guangdong Microbial Culture Collection Center (GDMCC), which is an International Depositary Authority under the Budapest Treaty. The deposited material has been accorded accession number GDMCC NO. 62409, with a deposit date of Apr. 23, 2022. All restrictions on the availability to the public of the deposited material will be irrevocably removed upon the granting of a patent, and the deposit will be maintained in accordance with the requirements of the Budapest Treaty and applicable U.S. patent regulations.

A medium for the MEFLC line includes the following components: high-sugar Dulbecco's Modified Eagle Medium (DMEM) (Gibco, C11995500BT), fetal bovine serum (FBS) with a volume content of 10% (Excell BIO, FSP500), non-essential amino acid (NEAA) with a volume content of 1% (Solarbio, P1400), PS with a volume content of 1% (Solarbio, N1250), and doxycycline hyclate (Dox) (Sangon, A600889-0025), where a final concentration of Dox in the medium is 2 μg/mL.

The present disclosure also provides a construction method for the MEFLC line, including the following steps:
1) constructing an MYOG gene-containing lentivirus, where the lentivirus can be a lentivirus carrying a tetracycline-inducible system or other inducible system which requires the change in the corresponding inducer when the expression of an MYOG gene is induced;
2) infecting a human iPSC line with the lentivirus, inducing the expression of an MYOG gene, and screening out a positive monoclonal cell line;
3) subjecting the positive monoclonal cell line to expanded cultivation, during which the expression of the MYOG gene is continuously induced; and 4) changing cultivation conditions, continuously inducing the expression of the MYOG gene, and screening out positive monoclonal cell lines to ensure the purity of MYOG-positive cells until the cell morphology changes significantly into fibroblastoid cells to obtain the MEFLC line.

The present disclosure explores the function of MEFLC through experiments.

MEFLC can resist hypoxia ($CoCl_2$), reactive oxygen species (ROS) ($H_2O_2$), and cytotoxicity of an antitumor drug (doxorubicin). The MEFLC line can be used as an additive for reducing an apoptosis proportion when a cryopreserved cardiomyocyte is resuscitated.

MEFLC can be co-cultivated with a human induced pluripotent stem cell-derived cardiomyocyte (hiPSC-CM) to protect hiPSC-CM under hypoxia ($CoCl_2$), ROS ($H_2O_2$), or antitumor drug (doxorubicin) treatment. The MEFLC line can be used as a support cell drug in the treatment of a CVD caused by cardiomyocyte apoptosis through cardiomyocyte infusion, and the injection of a mixture of the MEFLC line and a cardiomyocyte can reduce cardiomyocyte apoptosis to ensure a therapeutic effect.

MEFLC can reduce an apoptosis proportion in cryopreserved hiPSC-CMs after resuscitation. The MEFLC line can be used as an additive for reducing an apoptosis proportion in a hypoxia/ROS/doxorubicin environment.

MEFLC can improve the resistance of hiPSC-CM to a viral infection.

MEFLC can promote the sarcomere development and cell volume growth of hiPSC-CM.

MEFLC can significantly promote the survival of hiPSC-CM in mouse heart tissue.

MEFLC can significantly reduce the collagen volume fraction (CVF) in the heart tissue of an MI mouse and prevent a ventricular wall from thinning after MI. The MEFLC line can be used in the preparation of an injectable drug for treating MI.

BRIEF DESCRIPTION OF THE DRAWINGS

FIGS. 7A-7C show that the injection of MEFLC can significantly reduce the CVF in a heart of an MI mouse; and FIGS. 8A-8B show that the injection of MEFLC can significantly increase the thickness of a ventricular wall of an MI mouse.

DETAILED DESCRIPTION OF THE EMBODIMENTS

Figures 1A, 1B, 1C, 1D, 2:
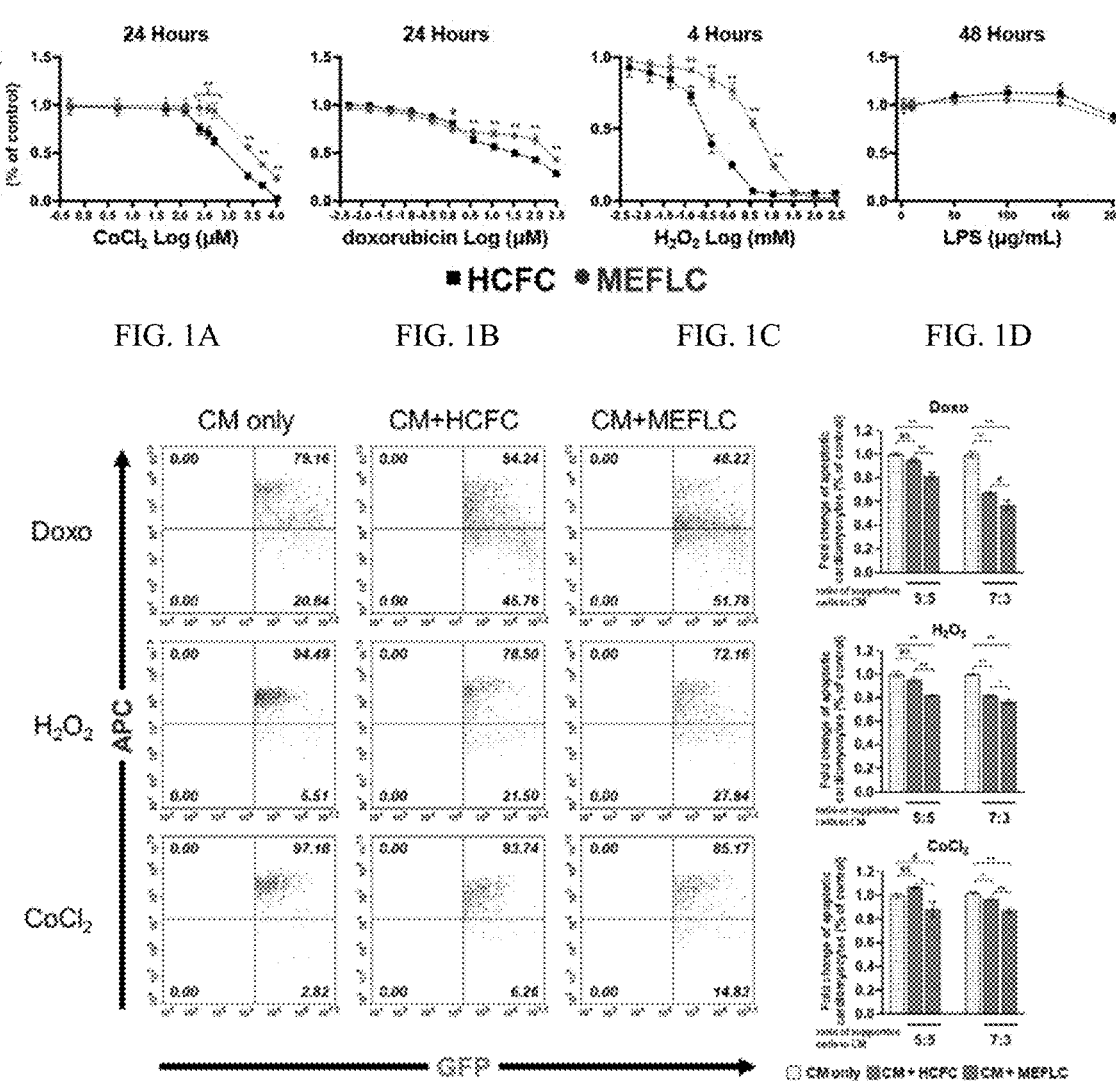
FIGS. 1A-1D show relative cell viability curves of human cardiac fibroblast cells (HCFCs) and MEFLCs under treatments with $CoCl_2$, $H_2O_2$, and doxorubicin at different concentrations.
FIG. 2 shows that the co-cultivation of MEFLC and hiPSC-CM can reduce the increase in cardiomyocyte apoptosis caused by $CoCl_2$, $H_2O_2$, and doxorubicin.

To allow those skilled in the art to understand the present disclosure more clearly and intuitively, the present disclosure is further described below by referring to the accompanying drawings.

1. MEFLC construction steps:

1.1 Construction of a pCW-MYOG-T2A-Puro lentiviral vector: MYOG cDNA and a puromycin resistance gene were subcloned into a pCW-Cas9-Blast vector (Addgene, 83481) by a conventional molecular cloning method to replace Cas9 and Blast genes in the original vector to obtain pCW-MYOG.

1.2 Lentivirus package:

1.2.1 HEK293T cells were inoculated into a 6-well plate and cultivated with a D10 medium (DMEM+FBS with a volume content of 10%) until cell confluency reached 70% to 80% ready for transfection.

1.2.2 The original medium was removed 1 h before transfection, and a pre-warmed serum-free OptiMEM medium was added at 2 mL/well.

1.2.3 The transfection was conducted with a Lipofectamine 2000 reagent according to product instructions. The HEK293T cells were co-transfected with pCW-MYOG (20 μg), pVSVg (10 μg) (Addgene), and psPAX2 (15 μg) (Addgene).

1.2.4 6 h later, the original medium was changed to a medium including DMEM, FBS with a volume content of 10%, and BSA with a volume content of 1%.

1.2.5 The cells were further cultivated for about 60 h, and a culture was collected and centrifuged at 3,000 rpm and 4° C. for 10 min to remove cell debris.

1.2.6 A resulting supernatant was filtered through a 0.45 μm low protein binding filter membrane (Millipore Steriflip HV/PVDF) to remove cell debris.

1.2.7 A resulting virus-containing filtrate was mixed with a sucrose buffer of a mass percentage content of 10% (50 mM Tris-HCl, pH 7.4, 100 mM NaCl, 0.5 mM EDTA) in a volume ratio of 4:1. The resulting mixture was added to a centrifuge tube and centrifuged at 10,000 g and 4° C. for 4 h. The resulting supernatant was carefully discarded, the centrifuge tube was drained on absorbent paper for 3 min, PBS was added for resuspension, and the resulting suspension was stored at −80° C.

1.3 Infection of a human iPSC line (DYR0100) with the pCW-MYOG-T2A-Puro lentivirus:

1.3.1 Cultivation of hiPSCs: The hiPSC DYR0100 (ATCC) was inoculated on a plate coated with Matrigel matrix (Corning, 354277) and then cultivated with STEMUP (Nissan Chemical Corporation). The STEMUP medium was changed every 2 days. iPSCs were passaged every 3 days or the cell passaging was conducted when cell confluency reached 80% to 90%. During the passaging, collected cells were rinsed once with 1×DPBS (Gibco, 14040133) and then treated with 0.5 mM EDTA (Invitrogen, 15575020) diluted by 1×DPBS (Gibco, 14190144) for 10 min at room temperature. A passage ratio was 1:3 to 1:6.

1.3.2 Transfection: The transfection was conducted when a confluency of hiPSCs reached 70% to 80% with a multiplicity of infection (MOI) of about 0.3 to 0.5. 24 h after the transfection; the medium was replaced with fresh STEMUP (with Dox at a final concentration of 2 μg/mL). 2 d later, the medium was replaced by STEMUP (with 2 μg/mL Dox+ puromycin (InvivoGen)) for screening. After 2 d to 3 d of screening, a transformation efficiency of about 30% was achieved. Single clones were picked and inoculated into different dishes to obtain the hiPSC-MYOG cell line. 24 h later, Dox was added to induce the expression of MYOG, and 48 h later, puromycin was added (final concentration: 2 μg/mL) for screening. The screening process lasted 48 h to 72 h, and viable monoclones were picked for expanded cultivation.

1.4 Quantitative real-time polymerase chain reaction (qRT-PCR) was used to identify whether MYOG was expressed in monoclones. Positive monoclones (named hiPSC-MYOG) were subjected to expanded cultivation, where Dox was added to a medium for continuously inducing the expression of MYOG, and the day was set as day 1. Medium: StemUp medium. Cultivation condition: (1) StemUp medium+Dox (final concentration: 2 μg/mL).

1.5 The hiPSC-MYOG was cultivated under cultivation condition (1) for 15 d to 20 d, and the hiPSC-MYOG was further cultivated under cultivation condition (2). Cultivation condition (2) was as follows: high-sugar DMEM+FBS with a volume content of 10%+NEAA with a volume content of 1%+PS with a volume content of 1%+Dox (final concentration: 2 μg/mL). Screening was conducted for 3 d to 4 d with puromycin (final concentration: 2 μg/mL) every 10 d to 14 d to ensure the purity of MYOG-positive cells. From day 30 to day 40, the cell morphology changed significantly into fibroblastoid cells and became fibroblast-like, and the fibroblast-like cells were named MEFLC.

1.6 MEFLC was cultivated under cultivation condition (2).

2. Functional analysis of MEFLC 2.1 MEFLC can resist hypoxia (CoCl$_2$), ROS (H$_2$O$_2$), and cytotoxicity of an antitumor drug (doxorubicin).

Compared with a human cardiac fibroblast cell (HCFC) line, MEFLC exhibits higher tolerance to hypoxia (CoCl$_2$), ROS (H$_2$O$_2$), and an antitumor drug (doxorubicin), and thus can be used for treating MI, heart failure, CHD, or the like.

2.1.1 Preparation of experimental materials: MEFLC was cultivated under cultivation condition (2); and HCFC was cultivated under cultivation condition (3). Cultivation condition (3) was as follows: high-sugar DMEM+FBS with a volume content of 10%+NEAA with a volume content of 1%+PS with a volume content of 1%.

2.1.2 Cell inoculation: When growing to a confluency of about 80%, MEFLC or HCFC was digested with 0.05% trypsin. The resulting cell suspension was collected and centrifuged at 200 g for 5 min, and the resulting cell pellet was resuspended with an appropriate volume of a medium, counted, and then inoculated into a 96-well plate at 10,000 cells/well.

2.1.3 Drug treatment: 24 h after the inoculation, Doxo, CoCl$_2$, H$_2$O$_2$, and LPS were added for drug treatments. 8 replicates were set for each drug treatment at each treatment concentration.

The Doxo treatment was conducted for 24 h under the following concentration gradient: 0 μM, 0.004 μM, 0.01 μM, 0.04 μM, 0.13 μM, 0.41 μM, 1.23 μM, 3.7 μM, 11.1 μM, 33.3 μM, 100 μM, and 300 μM.

The CoCl$_2$ treatment was conducted for 24 h under the following concentration gradient: 0 μM, 1.33 μM, 4 μM, 13 μM, 41 μM, 123 μM, 370 μM, 1.11 mM, 3.33 mM, 10 mM, and 30 mM.

The H$_2$O$_2$ treatment was conducted for 4 h under the following concentration gradient: 0 mM, 0.004 mM, 0.01 mM, 0.04 mM, 0.13 mM, 0.41 mM, 1.23 mM, 3.7 mM, 11.1 mM, 33.3 mM, 100 mM, and 300 mM.

The LPS treatment was conducted for 48 h under the following concentration gradient: 0 μg/mL, 2 μg/mL, 10 μg/mL, 50 μg/mL, 100 μg/mL, 150 μg/mL, and 200 μg/mL.

2.1.4 Cell viability detection: Cell viability was detected with a PrestoBlue cell viability assay reagent (Invitrogen, A13261).

2.1.5 Experimental results and analysis: After the treatments with high-concentration CoCl$_2$ (123 μM to 30 mM), high-concentration Doxo (3.7 μM to 300 μM), medium-concentration H$_2$O$_2$ (0.04 mM to 11.1 mM), and 150 μg/mL LPS, the cell viability of MEFLC was significantly higher than the cell viability of HCFC.

As shown in FIGS. 1A-1D, MEFLC exhibits high tolerance to CoCl$_2$, H$_2$O$_2$, and Doxo.

2.2 MEFLC can be co-cultivated with hiPSC-CM to protect hiPSC-CM under a hypoxia (CoCl$_2$), ROS (H$_2$O$_2$), or antitumor drug (doxorubicin) treatment.

Control groups: hiPSC-CM was co-cultivated with HCFC (CM+HCFC), and hiPSc-CM was cultivated alone (CM).

Experimental group: hiPSC-CM was co-cultivated with MEFLC (CM+MEFLC).

Compared with the control groups, the proportion of apoptotic cells in the CM+MEFLC group was significantly reduced under the treatments with CoCl$_2$, H$_2$O$_2$, and doxorubicin.

2.2.1 Preparation of experimental materials: MEFLC was cultivated under cultivation condition (2) until confluency reached about 80%, then treated with mitomycin (20 μg/mL) for 5 h, and then further cultivated under cultivation condition (2). The resulting cell was named MEFLC-Mito-C. HCFC was cultivated under cultivation condition (3) until confluency reached about 80%, then treated with mitomycin (20 μg/mL) for 5 h, and then further cultivated under cultivation condition (3), and the resulting cell was named HCFC-Mito-C. To facilitate the subsequent flow cytometry (FCM) analysis, hiPSC-CM was labeled with a green fluorescent protein (GFP), then infected with AAV-EGFP (MOI=2) (an infection efficiency was higher than 98%), and then further cultivated under cultivation condition (4), and the resulting cell was named hiPSc-CM-EGFP. Cultivation condition (4) was as follows: high-sugar DMEM+KOSR with a volume content of 3%+NEAA with a volume content of 1%+PS with a volume content of 1%.

2.2.2 Co-cultivation of cells: HCFC/MEFLC and hiPSC-CM were co-cultivated under cultivation condition (3) according to HCFC/MEFLC: hiPSC-CM=7:3 and HCFC/MEFLC: hiPSC-CM=5:5, and a group with only hiPSC-CM was set as a control group, where the groups had the same total number of cells. A specific method was as follows: CM group: hiPSC-CM-EGFP was inoculated into a 12-well plate at 2.5×10$^5$ cells/well; CM+HCFC (7:3) group: iPSc-CM-EGFP was inoculated at 7.5×10$^4$ cells/well and HCFC-Mito-C was inoculated at 1.75×10$^5$ cells/well into a 12-well plate; CM+MEFLC (7:3) group: iPSC-CM-EGFP was inoculated at 7.5×10$^4$ cells/well and MEFLC-Mito-C was inoculated at 1.75×10$^5$ cells/well into a 12-well plate; CM+HCFC (5:5) group: iPSC-CM-EGFP and HCFC-Mito-C each were inoculated into a 12-well plate at 1.25×10$^5$ cells/well; and CM+MEFLC (5:5) group: iPSc-CM-EGFP and MEFLC-Mito-C each were inoculated into a 12-well plate at 1.25×10$^5$ cells/well. The medium for the cultivation of cells was changed every 2 d to 3 d.

2.2.3 Drug treatment: 4 d after the co-cultivation, different drug treatments were conducted, where a Doxo treatment was conducted for 24 h at a Doxo concentration of 1 μM; a CoCl$_2$ treatment was conducted for 24 h at a CoCl$_2$ concentration of 1 mM; a H$_2$O$_2$ treatment was conducted for 4 h at a H$_2$O$_2$ concentration of 1 mM; 3 to 4 biological replicates were set for each group; and no drug treatment was conducted in a control group.

2.2.4 Apoptosis detection: An APCAnnexinV apoptosis detection kit (Biolegend, 640920) was used to detect an apoptosis proportion (APC positive) of cardiomyocytes (GFP positive) in each group after the different drug treatments.

2.2.5 Experimental results and analysis: As shown in FIG. 2, after the Doxo, $CoCl_2$, and $H_2O_2$ treatments, the apoptosis proportion in the CM+MEFLC group of either 7:3 or 5:5 was decreased significantly compared with the CM group and the CM+HCFC group. It indicates that MEFLC can protect hiPSC-CM under hypoxia ($CoCl_2$), ROS ($H_2O_2$), and antitumor drug (doxorubicin) treatments.

2.3 MEFLC can reduce an apoptosis proportion in cryopreserved hiPSC-CMs after resuscitation.

2.3.1 Preparation of experimental materials: MEFLC was cultivated under cultivation condition (2) until confluency reached about 80%, then treated with mitomycin (20 μg/mL) for 5 h, and then further cultivated under cultivation condition (2), and a resulting cell was named MEFLC-Mito-C. HCFC was cultivated under cultivation condition (3) until confluency reached about 80%, then treated with mitomycin (20 μg/mL) for 5 h, and then further cultivated under cultivation condition (3), and a resulting cell was named HCFC-Mito-C. hiPSC-CM was infected with AAV-EGFP (MOI=2) (an infection efficiency was higher than 98%, and a resulting cell was named hiPSC-CM-EGFP), then cultivated under cultivation condition (4) for 3 d, digested with 0.05% trypsin, cryopreserved with a cell cryopreservation solution STEMdiff, and stored in liquid nitrogen.

2.3.2 Resuscitation and co-cultivation of cells: hiPSC-CM-EGFP was quickly taken out from liquid nitrogen and thawed in a 37° C. water bath, an equal volume of a medium was quickly added, and the resulting mixture was centrifuged at 200 g for 5 min. The resulting cell pellet was collected, resuspended with an appropriate volume of a medium, and counted. MEFLC-Mito-C and HCFC-Mito-C each were digested with 0.05% trypsin, resulting suspensions each were centrifuged at 200 g for 5 min, and resulting cell pellets each were collected, resuspended with an appropriate amount of a medium, and counted. HCFC/MEFLC and iPSC-CM were co-cultivated under cultivation condition (3) according to HCFC/MEFLC: iPSC-CM=7:3, and a group with only hiPSC-CM was set as a control group, where the groups had the same total number of cells. A specific method was as follows: CM group: hiPSC-CM-EGFP was inoculated into a 12-well plate at $2.5 \times 10^5$ cells/well; CM+HCFC group: hiPSc-CM-EGFP was inoculated at $7.5 \times 10^4$ cells/well, and HCFC-Mito-C was inoculated at $1.75 \times 10^5$ cells/well into a 12-well plate; CM+MEFLC group: iPSC-CM-EGFP was inoculated at $7.5 \times 10^4$ cells/well and MEFLC-Mito-C was inoculated at $1.75 \times 10^5$ cells/well into a 12-well plate. 3 to 4 biological replicates were set for each group. 2 d after cultivation, the medium was changed. 4 d after cultivation, an apoptosis proportion of cardiomyocytes was detected.

2.3.3 Apoptosis detection: An APCAnnexinV apoptosis detection kit (Biolegend, 640920) was used to detect an apoptosis proportion (APC positive) of cardiomyocytes (EGFP positive) in each of the three groups.

Figures 3A, 3B, 4A, 4B:
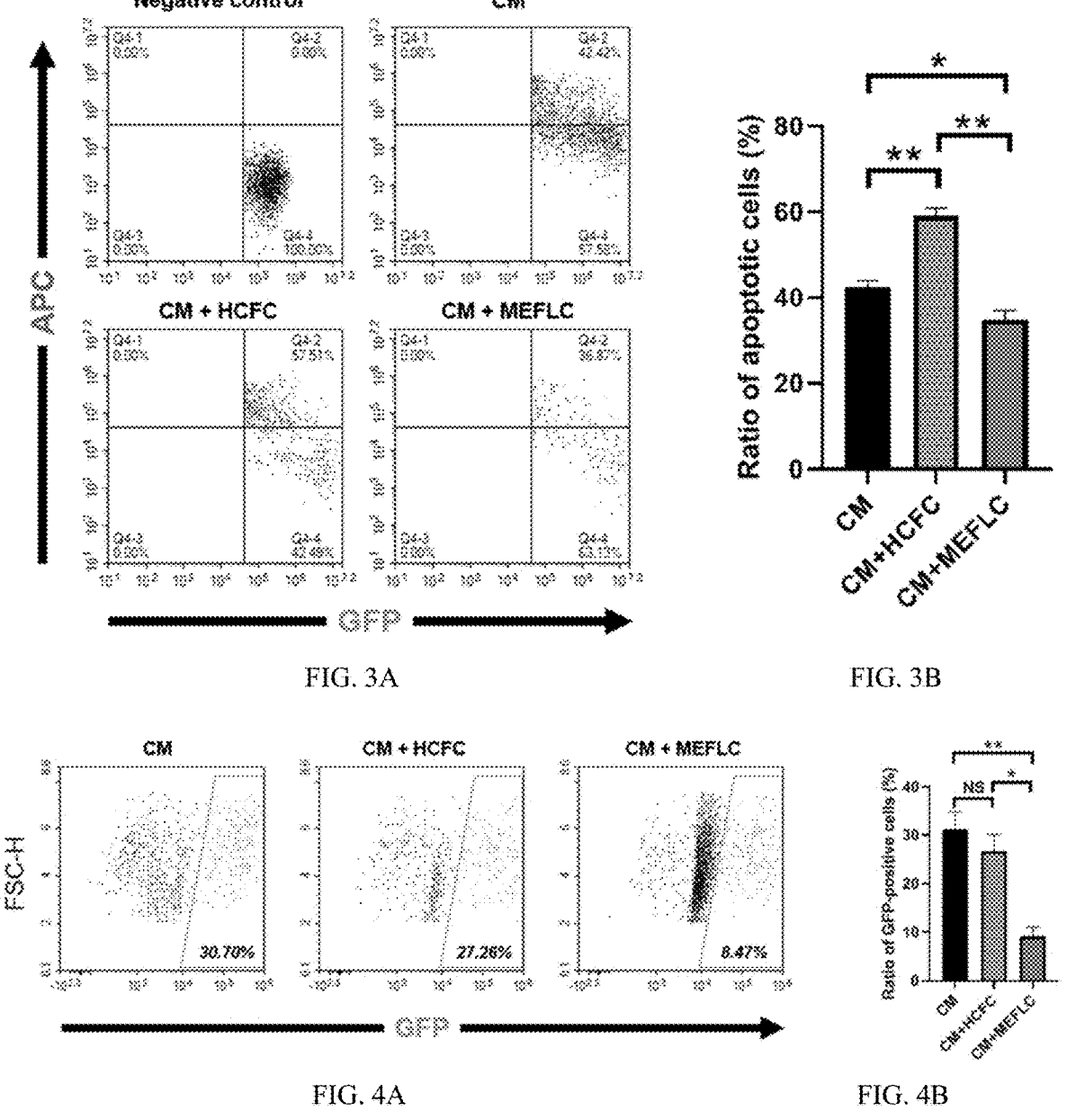
FIGS. 3A-3B show that MEFLC can reduce an apoptosis proportion in cryopreserved hiPSC-CMs after resuscitation.
FIGS. 4A-4B show that MEFLC can improve the resistance of hiPSC-CM to a viral infection.

2.3.4 Experimental results and analysis: As shown in FIGS. 3A-3B, compared with the CM group, an apoptosis proportion of cardiomyocytes in the CM+MEFLC group was decreased significantly (7.8%), while an apoptosis proportion of cardiomyocytes in the CM+HCFC group was increased significantly. It indicates that the co-cultivation of MEFLC and hiPSC-CM can reduce an apoptosis proportion in cryopreserved cardiomyocytes after resuscitation and improve the survival rate after resuscitation.

Data corresponding to CM, CM+HCFC, and CM+MEFLC in the histogram of FIGS. 3A-3B were as follows:

|  | CM | CM + HCFC | CM + MEFLC |
|---|---|---|---|
| ave | 42.57 | 59.09 | 34.81666667 |

2.4 MEFLC can improve the resistance of hiPSC-CM to a viral infection.

2.4.1 Preparation of experimental materials: MEFLC was cultivated under cultivation condition (2) until confluency reached about 80%, then treated with mitomycin (20 μg/mL) for 5 h, and then further cultivated under cultivation condition (2), and a resulting cell was named MEFLC-Mito-C. HCFC was cultivated under cultivation condition (3) until confluency reached about 80%, then treated with mitomycin (20 μg/mL) for 5 h, and then further cultivated under cultivation condition (3), and a resulting cell was named HCFC-Mito-C. hiPSC-CM was infected with AAV-mcherry (MOI=2) (a proportion of red fluorescent cells observed under a microscope was higher than 98%) and then cultivated under cultivation condition (4), and a resulting cell was named hiPSC-CM-mcherry.

2.4.2 Co-cultivation of cells: HCFC/MEFLC and hiPSC-CM were co-cultivated under cultivation condition (3) according to HCFC/MEFLC: hiPSC-CM=7:3, and a group with only hiPSC-CM was set as a control group, where the groups had the same total number of cells. A specific method was as follows: CM group: hiPSc-CM-mcherry was inoculated into a 12-well plate at $2.5 \times 10^5$ cells/well; CM+HCFC group: hiPSC-CM-mcherry was inoculated at $7.5 \times 10^4$ cells/well and HCFC-Mito-C was inoculated at $1.75 \times 10^5$ cells/well into a 12-well plate; CM+MEFLC group: hiPSC-CM-mcherry was inoculated at $7.5 \times 10^4$ cells/well and MEFLC-Mito-C was inoculated at $1.75 \times 10^5$ cells/well into a 12-well plate. 3 to 4 biological replicates were set for each group.

2.4.3 Viral infection: 3 d after cell cultivation, an adenovirus AAV-EGFP was used to infect co-cultivated cells according to MOI=0.5 (three groups: CM, CM+HCFC, and CM+MEFLC). 24 h after viral infection, a virus-containing culture supernatant was removed, and the cells were washed once with PBS and further cultivated under cultivation condition (3) for 48 h. A proportion of GFP-positive cardiomyocytes (GFP-positive cells were infected by the adenovirus AAV-EGFP) was detected by FCM.

2.4.4 Determination of a proportion of virus-infected cells: The cells were digested with 0.05% trypsin, the resulting suspension was centrifuged at 200 g for 5 min, and the resulting cell pellet was collected and resuspended with PBS to obtain a cell suspension. A proportion of virus-infected cardiomyocytes (namely, a proportion of GFP-positive cells in mcherry-positive cells) in each group was analyzed by FCM.

2.4.5 Experimental results and analysis: As shown in FIGS. 4A-4B, a proportion of GFP-positive cardiomyocytes in the CM+MEFLC group was decreased by 22.0% compared with the CM group, while a proportion of GFP-positive cardiomyocytes in the CM+HCFC group was not significantly different from a proportion of GFP-positive cardiomyocytes in the CM group. It indicates that the co-cultivation of MEFLC and CM can significantly improve the resistance of hiPSC-CM to a viral infection.

Data corresponding to CM, CM+HCFC, and CM+MEFLC in the histogram of FIGS. 4A-4B were as follows:

|  | CM | CM + HCFC | CM + MEFLC |
|---|---|---|---|
| Ave | 31.11 | 26.74333333 | 9.09 |

2.5 MEFLC can promote the sarcomere development and cell volume growth of hiPSC-CM.

Figure 5:
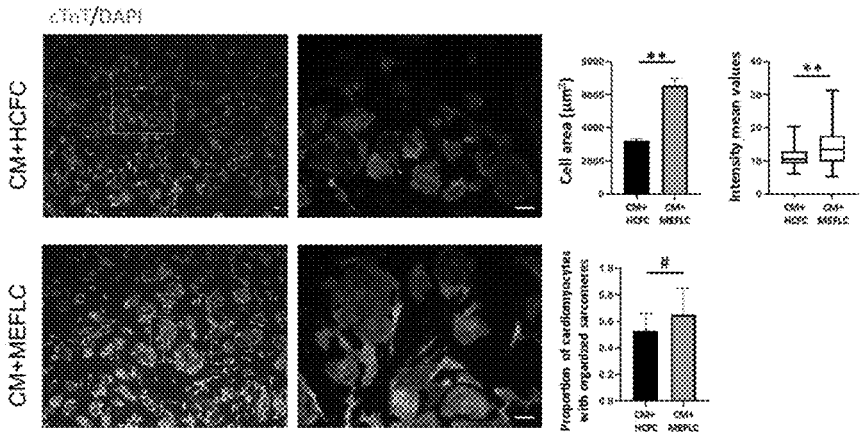
FIG. 5 shows that MEFLC can promote the sarcomere development and cell volume growth of hiPSC-CM.

As shown in FIG. 5, compared with the control group (HCFC and hiPSC-CM were co-cultivated, CM+HCFC group), after MEFLC and hiPSC-CM were co-cultivated for 1 week (CM+MEFLC group), a hiPSC-CM area was increased significantly ($p<0.001$), and a proportion of hiPSC-CM with an ordered sarcomere structure was increased significantly ($p<0.05$). It indicates that the co-cultivation of MEFLC and hiPSC-CM can promote the sarcomere development and volume growth of hiPSC-CM.

2.6 MEFLC can significantly promote the survival of hiPSC-CM in a mouse heart tissue.

Experimental Purpose

After a multi-point injection of fluorescently-labeled MEFLC and hiPSC-CM into a mouse myocardium, a fluorescence intensity change was detected to determine the survival time of cells in each group in the mouse myocardium.

Experimental Materials

Experimental cells: hiPSC-CM emitted green fluorescence after being infected with the lentivirus HBLV-Zs-Green-Puro, and MEFLC emitted red fluorescence after being infected with the lentivirus HBLV-mCherry-Puro.

Experimental animals: 18 male C57BL/6J mice each with a body weight of 20 g+2 g.

Experimental Scheme (1) Experimental grouping:

Experimental group 1: Multi-point injection of MEFLC+hiPSC-CM into the myocardium, n=6

Experimental group 2: Multi-point injection of hiPSC-CM into the myocardium, n=6

Control group: Multi-point injection of PBS (control group) into the myocardium, n=3

(2) Cell number:

Experimental group 1: MEFLC ($7\times10^5$ cells in total) and hiPSC-CM ($3\times10^5$ cells in total) were injected into each mouse at 3 sites.

Experimental group 2: hiPSC-CM ($3\times10^5$ cells in total) was injected into each mouse at 3 sites.

(3) Myocardial injection steps: a. Mice each were intraperitoneally injected with tribromoethanol (1.25%, 0.1 mL/10 g) for anesthesia, hair in a surgical area was removed, and endotracheal intubation was conducted. b. Each mouse was injected with 30 μL of normal saline (NS) or cells at the upper, middle, and lower points (triangular) of the left ventricle. c. The chest was closed, and the mice were kept warm for awakening.

(4) In vivo imaging steps:

1 d, 3 d, 7 d, 14 d, 21 d, and 28 d after the injection, in vivo imaging was conducted using a Slimaging small animal in vivo imaging system to detect the myocardial fluorescence expression in mice.

Before imaging, mice each were intraperitoneally injected with tribromoethanol (1.25%, 0.1 mL/10 g) for anesthesia, and then a small animal in vivo imager was inserted.

Detection of zs-Green fluorescence:

Excitation wavelength: 465 nm, Emission wavelength: 510 nm, and Exposure time: 60 s.

Experimental Results

Figure 6A:
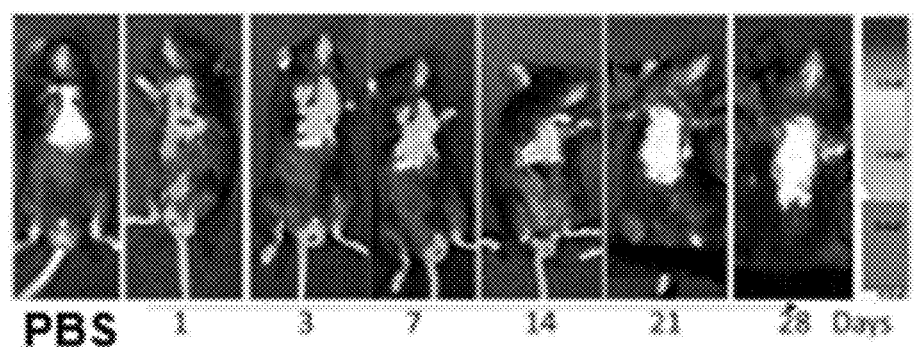
FIGS. 6A-6C show that MEFLC can significantly prolong the survival time of hiPSC-CM in a mouse heart tissue.
Figure 6B:
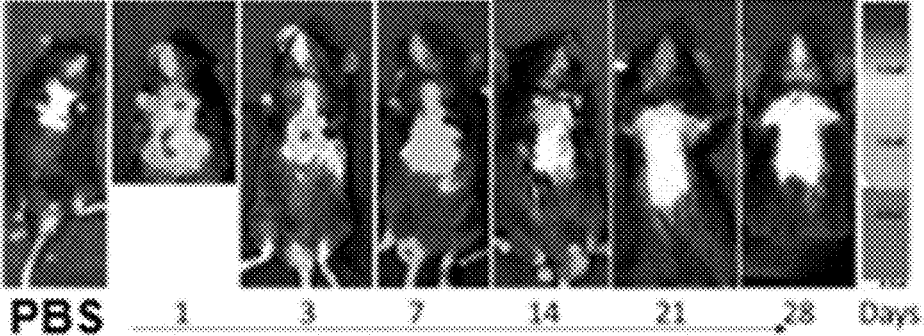
Figure 6C:
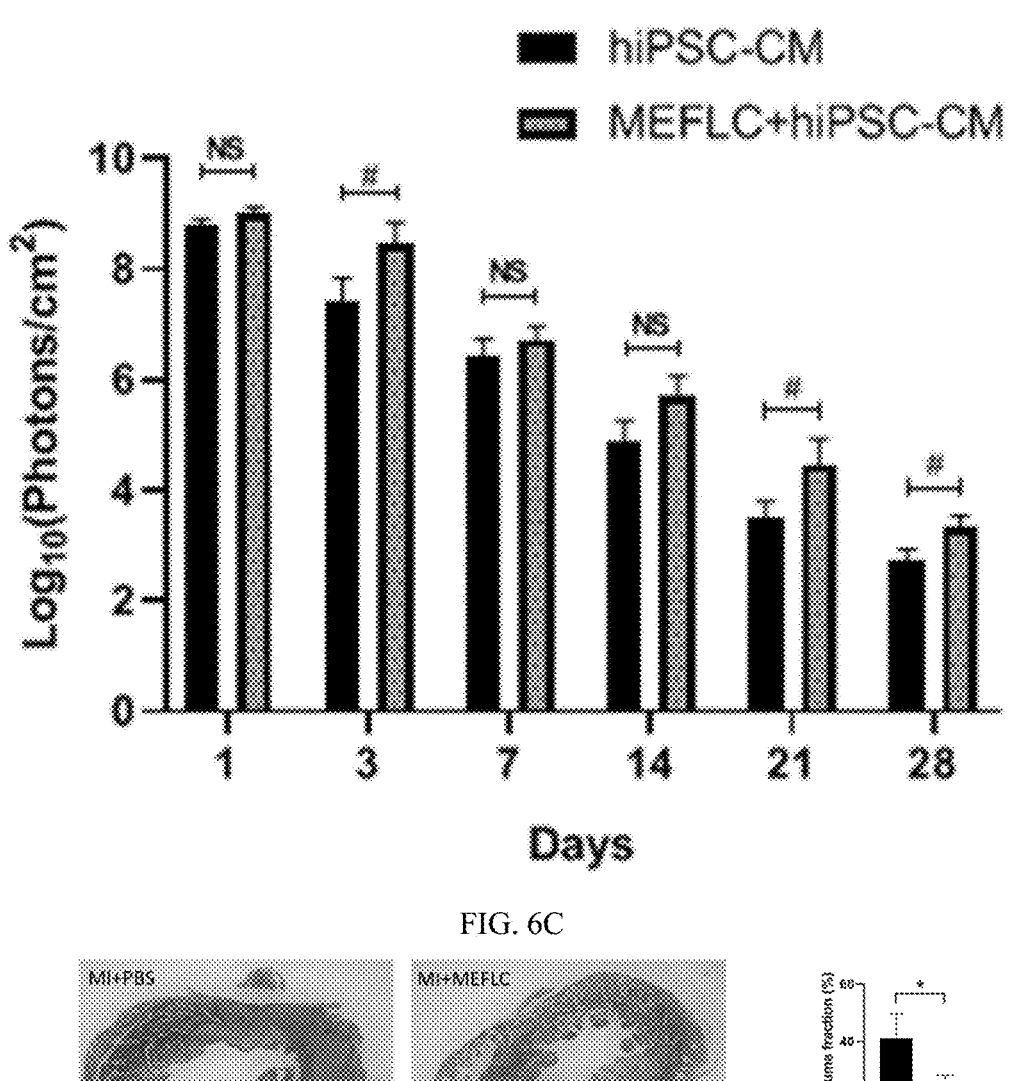

The change of the zs-Green fluorescence intensity of the mouse myocardial tissue over time was shown in FIGS. 6A-6C. 21 d and 28 d after the injection, the fluorescence intensity of the MEFLC+hiPSC-CM group was significantly higher than the fluorescence intensity of the hiPSC-CM group, indicating that the number of survival hiPSC-CM in the MEFLC+hiPSC-CM group was significantly larger than the number of survival hiPSC-CM in the hiPSC-CM group, that is, MEFLC promoted the survival of hiPSC-CM in the mouse heart tissue.

2.7 MEFLC can significantly reduce a CVF in the heart tissue of an MI mouse and prevent a ventricular wall from thinning after MI.

Experimental Purpose

The therapeutic effect of MEFLC on MI mice was investigated.

Experimental Materials

Experimental animals: 12 male C57BL/6J mice each with a body weight of 20 g+2 g.

Experimental Scheme (1) Experimental grouping:

Experimental group: MI group+myocardial injection of MEFLC (n=6)

Control group: MI group+myocardial injection of PBS (n=6)

(2) Cell number:

In the experimental group, $1\times10^6$ MEFLCs in total were injected into each mouse at 3 sites.

(3) Surgical modeling for MI mice: The mice each were intraperitoneally injected with tribromoethanol (1.25%, 0.1 mL/10 g) for anesthesia, hair in a surgical area was removed, and endotracheal intubation was conducted. The left chest was cut, the muscle was separated to expose ribs, an incision was provided in an intercostal space between the fourth and fifth ribs to expose the heart, and the anterior descending branch of the left coronary artery was permanently ligated with sutures to obtain an MI model. PBS or MEFLC (30 μL) was injected around the anterior descending branch of the left coronary artery. The chest was closed, and the mice were kept warm for awakening.

(4) On day 7 and day 28 after surgery, a mouse heart tissue was collected, sectioned, and subjected to HE and Masson staining, respectively.

Experimental Results (1) As shown in FIGS. 7A-7C, heart tissue sections of MI mice in the experimental group and control group 7 d after the surgery were subjected to Masson staining, scanning images were acquired for the pathological sections, and a CVF of each group was analyzed by ImageJ software. The average CVF of the experimental group (21.51%) was significantly lower than the average CVF of the control group (41.14%), n=6, p=0.0065.

(2) As shown in FIGS. 8A-8B, heart tissue sections of MI mice in the experimental group and control group 28 d after the surgery were subjected to HE staining, and scanning images were acquired for the pathological sections. Compared with the experimental group, the ventricular wall of the control group was significantly thinned (a black arrow in the figure indicates a thinned part of the ventricular wall). It is believed that the injection of MEFLC alone can inhibit the apoptosis of cardiomyocytes, and the results in FIGS. 8A-8B also show that the injection of MEFLC alone into MI mice can reduce the thinning of the ventricular wall, which means that the number of dead cardiomyocytes after MI is reduced.

What is claimed is:

1. A myogenin-expressing fibroblast-like cell (MEFLC) line deposited in the Guangdong Microbial Culture Collection Center (GDMCC) on Apr. 23, 2022 with an accession number of GDMCC NO: 62409.

2. A medium for cultivating the MEFLC line according to claim 1, comprising: high-sugar Dulbecco's Modified Eagle Medium (DMEM), fetal bovine serum (FBS) with a volume content of 10%, non-essential amino acid (NEAA) with a volume content of 1%, PS with a volume content of 1%, and doxycycline hyclate (Dox), wherein a final concentration of the Dox in the medium is 2 µg/mL.

3. A construction method for the MEFLC line according to claim 1, comprising the following steps:

1) Constructing an MYOG gene-containing lentivirus;

2) Infecting a human induced pluripotent stem cell (iPSC) line with the MYOG gene-containing lentivirus, inducing an expression of an MYOG gene, and screening out a first positive monoclonal cell line;

3) Subjecting the first positive monoclonal cell line to an expanded cultivation, and continuously inducing the expression of the MYOG gene; and 4) Changing cultivation conditions, continuously inducing the expression of the MYOG gene, and screening out a second positive monoclonal cell line to ensure a purity of MYOG-positive cells until a cell morphology of the MYOG-positive cells changes significantly into fibroblastoid cells to obtain the MEFLC line.

4. The construction method according to claim 3, wherein in step 1), the MYOG gene-containing lentivirus is a lentivirus carrying a tetracycline-inducible system; and the MYOG gene-containing lentivirus is a pCW-MYOG-T2A-Puro lentivirus, and a construction method for the pCW-MYOG-T2A-Puro lentivirus comprises:

1) Construction of a lentiviral expression vector: subcloning MYOG cDNA and a puromycin resistance gene into a pCW-Cas9-Blast vector through a conventional molecular cloning method to replace Cas9 and Blast genes in the pCW-Cas9-Blast vector to obtain a pCW-MYOG plasmid; and 2) Lentivirus package:

A. inoculating HEK293T cells into a 6-well plate and cultivating the HEK293T cells with a D10 medium until a cell confluency reaches 70% to 80% ready for a transfection, wherein the D10 medium comprises DMEM and FBS with a volume content of 10%;

B. 1 h before the transfection, removing the D10 medium and adding a pre-warmed serum-free OptiMEM medium at 2 mL/well;

C. using a Lipofectamine 2000 reagent to co-transfect the HEK293T cells with pCW-MYOG, pVSVg, and psPAX2 according to product instructions;

D. changing the pre-warmed serum-free OptiMEM medium to a medium comprising DMEM, FBS with a volume content of 10%, and bovine serum albumin (BSA) with a volume content of 1%;

E. further cultivating the HEK293T cells for 60 h, and collecting and centrifuging a culture at 3,000 rpm and 4° C. for 10 min to remove cell debris to obtain a first resulting supernatant;

F. filtering the first resulting supernatant through a 0.45 µm low protein binding filter membrane to remove cell debris to obtain a virus-containing filtrate; and G. mixing the virus-containing filtrate and a sucrose buffer with a mass percentage content of 10% in a volume ratio of 4:1 to obtain a resulting mixture, adding the resulting mixture to a centrifuge tube, and centrifuging at 10,000 g and 4° C. for 4 h, wherein the sucrose buffer comprises 50 mM Tris-Hcl, 100 mM NaCl, and 0.5 mM EDTA and has a pH of 7.4; and discarding a second resulting supernatant, draining the centrifuge tube on absorbent paper for 3 min, adding PBS for a resuspension, and storing a resulting suspension at −80° C.

5. The construction method according to claim 4, wherein an inducer for inducing the expression of the MYOG gene is Dox; and each of the first positive monoclonal cell line and the second positive monoclonal cell line is screened out by adding puromycin to a medium.

6. The construction method according to claim 3, wherein a medium for the expanded cultivation of the first positive monoclonal cell line is a StemUp medium.

7. The construction method according to claim 3, wherein the step of changing the cultivation conditions comprises using a medium comprising high-sugar DMEM, FBS with a volume content of 10%, NEAA with a volume content of 1%, PS with a volume content of 1%, and Dox, wherein a final concentration of the Dox in the medium is 2 µg/mL.

8. A method of a use of the MEFLC line according to claim 1 in a preparation of a drug for treating a cardiovascular disease (CVD) caused by cardiomyocyte apoptosis, comprising:

using the MEFLC line as a support cell drug for a cardiomyocyte infusion by mixing the MEFLC line with a cardiomyocyte for injection or using the MEFLC line alone for injection;

wherein a dosage form of the drug is an injection; and the CVD caused by the cardiomyocyte apoptosis is myocardial infarction (MI), heart failure, or coronary heart disease (CHD).

9. A method of a use of the MEFLC line according to claim 1 as an additive for reducing an apoptosis proportion when a cryopreserved cardiomyocyte is resuscitated or a cardiomyocyte is in a hypoxia/reactive oxygen species (ROS)/doxorubicin environment.

10. A method of a use of the MEFLC line according to claim 1 in a preparation of an injectable drug for treating MI, heart failure, or CHD.

11. The construction method according to claim 4, wherein a medium for the expanded cultivation of the first positive monoclonal cell line is a StemUp medium.

12. The construction method according to claim 5, wherein a medium for the expanded cultivation of the first positive monoclonal cell line is a StemUp medium.

13. The construction method according to claim 4, wherein the step of changing the cultivation conditions comprises using a medium comprising high-sugar DMEM, FBS with a volume content of 10%, NEAA with a volume content of 1%, PS with a volume content of 1%, and Dox, wherein a final concentration of the Dox in the medium is 2 µg/mL.

14. The construction method according to claim 5, wherein the step of changing the cultivation conditions comprises using a medium comprising high-sugar DMEM, FBS with a volume content of 10%, NEAA with a volume content of 1%, PS with a volume content of 1%, and Dox, wherein a final concentration of the Dox in the medium is 2 µg/mL.

* * * * *